United States Patent
Palmer et al.

(10) Patent No.: US 9,870,165 B2
(45) Date of Patent: *Jan. 16, 2018

(54) BACK-UP AND RESTORATION OF DATA BETWEEN VOLATILE AND FLASH MEMORY

(71) Applicant: International Business Machines Corporation, Armonk, NY (US)

(72) Inventors: Michael J. Palmer, Southampton (GB); Kelvin Wong, Eastleigh (GB)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/434,432

(22) Filed: Feb. 16, 2017

(65) Prior Publication Data

US 2017/0220276 A1 Aug. 3, 2017

Related U.S. Application Data

(63) Continuation of application No. 14/822,140, filed on Aug. 10, 2015, now Pat. No. 9,632,715.

(51) Int. Cl.
G06F 3/06 (2006.01)
G06F 12/08 (2016.01)
G06F 12/0868 (2016.01)

(52) U.S. Cl.
CPC ............ *G06F 3/0619* (2013.01); *G06F 3/065* (2013.01); *G06F 3/0688* (2013.01); *G06F 12/0868* (2013.01); *G06F 2212/1032* (2013.01)

(58) Field of Classification Search
CPC ...... G06F 3/0619; G06F 3/065; G06F 3/0688; G06F 12/0868; G06F 2212/1038;
(Continued)

(56) References Cited

U.S. PATENT DOCUMENTS 5,802,551 A 9/1998 Komatsu et al.
7,856,528 B1 12/2010 Frost et al.
(Continued)

FOREIGN PATENT DOCUMENTS

EP 2249243 A1 11/2010
EP 2299363 A1 3/2011
(Continued)

OTHER PUBLICATIONS

Boukhobza et al., "A Cache Management Strategy to Replace Wear Leveling Techniques for Embedded Flash Memory", International Symposium on Performance Evaluation of Computer & Telecommunication Systems (SPECTS) 2011, Jun. 27-30, 2011, The Hague, pp. 1-8, <http://ieeexplore.ieee.org/xpl/articleDetails.jsp?tp=&arnumber=5984840&contentType=Conference+Publications&searchWithin%3DWear+Leveling+Technique%26queryText%3DNAND+Flash+Memory+Technology>.
(Continued)

*Primary Examiner* — Aracelis Ruiz
(74) *Attorney, Agent, or Firm* — James H. Mayfield

(57) ABSTRACT

A method and system are provided for back-up and restoration of data between volatile and flash memory. The method for controlling back-up of data to flash memory includes: organizing back-up data into stripes, wherein a stripe is a set of pages across all available flash memory devices, dies and planes which have the same block and page address; maintaining metadata indicating locations of known bad planes and grown bad planes; using the metadata when writing back-up data to determine which planes to send cache program commands to; and sending cache program commands to three or more stripes of data simultaneously including providing an indication in the stripe that the stripe is handling a cache program command. If a grown bad block is encountered whilst saving a stripe of data, the stripe
(Continued)

of data is re-written to the next available page address avoiding the grown bad block.

20 Claims, 12 Drawing Sheets

(58) Field of Classification Search
CPC ....... G06F 2212/2022; G06F 2212/222; G06F 2212/7209
See application file for complete search history.

(56) References Cited

U.S. PATENT DOCUMENTS

| | | | |
|---|---|---|---|
| 8,103,821 B2 | 1/2012 | Chang et al. | |
| 8,112,573 B2 | 2/2012 | Keays | |
| 8,169,839 B2 | 5/2012 | Moshayedi et al. | |
| 8,200,885 B2 | 6/2012 | Sartore | |
| 8,200,929 B1 | 6/2012 | Sartore | |
| 8,566,639 B2 | 10/2013 | Moshayedi et al. | |
| 8,819,337 B1 | 8/2014 | Oshinsky et al. | |
| 9,053,012 B1 | 6/2015 | Northcott et al. | |
| 9,501,356 B2 | 11/2016 | Palmer et al. | |
| 9,501,404 B2 | 11/2016 | Palmer et al. | |
| 2006/0015683 A1 | 1/2006 | Ashmore et al. | |
| 2006/0239075 A1 | 10/2006 | Williams et al. | |
| 2007/0061538 A1 | 3/2007 | Chang et al. | |
| 2007/0113000 A1* | 5/2007 | Murin | G11C 16/26 711/103 |
| 2008/0256420 A1 | 10/2008 | Hafner et al. | |
| 2009/0161435 A1 | 6/2009 | Park | |
| 2009/0172335 A1 | 7/2009 | Kulkarni et al. | |
| 2009/0240873 A1 | 9/2009 | Yu et al. | |
| 2009/0282301 A1 | 11/2009 | Flynn et al. | |
| 2010/0122148 A1 | 5/2010 | Flynn et al. | |
| 2010/0202239 A1 | 8/2010 | Moshayedi et al. | |
| 2010/0318844 A1 | 12/2010 | Matsuda et al. | |
| 2011/0093650 A1 | 4/2011 | Kwon et al. | |
| 2011/0302445 A1 | 12/2011 | Byom et al. | |
| 2012/0023365 A1 | 1/2012 | Byom et al. | |
| 2012/0151254 A1 | 6/2012 | Horn | |
| 2012/0159289 A1 | 6/2012 | Piccirillo et al. | |
| 2012/0185738 A1 | 7/2012 | Gyllenskog et al. | |
| 2012/0236656 A1 | 9/2012 | Cometti | |
| 2012/0239976 A1 | 9/2012 | Cometti et al. | |
| 2012/0262815 A1 | 10/2012 | Sundrani | |
| 2013/0163335 A1 | 6/2013 | Kim et al. | |
| 2013/0173954 A1 | 7/2013 | Woo et al. | |
| 2014/0281174 A1 | 9/2014 | Lee | |

FOREIGN PATENT DOCUMENTS

| | | |
|---|---|---|
| GB | 2507691 A | 5/2014 |
| GB | 2517435 A | 2/2015 |
| TW | 201428757 A | 7/2014 |
| WO | 2012100087 A2 | 7/2012 |
| WO | 2014075823 A1 | 5/2014 |
| WO | 2014120140 A1 | 8/2014 |

OTHER PUBLICATIONS

Chang et al., "Efficient Wear Leveling in NAND Flash Memory", Inside Solid State Drives (SSDs), Springer Series in Advanced Microelectronics 37, Chapter 9, pp. 233-257, DOI 10.1007/978-94-007-5146-0 9, © Springer ScienceCBusiness Media Dordrecht 2013.
Yun et al., "Bloom Filter-based Dynamic Wear Leveling for Phase-Change RAM", Design, Automation & Test in Europe Conference & Exhibition, Mar. 12-16, 2012, Dresden, DOI: 10.1109/DATE. 2012.6176713, pp. 1-6, <http://ieeexplore.ieee.org/xpl/articleDetails.jsp?tp=&arnumber=6176713&contentType=Conference+Publications&searchWithin%3DWear+Leveling%26queryText%3DNAND+Flash+Memory+Technology>.
"Patent Act 1977: Search Report under Sectio 17(5)", Intellectual Property Office, Application No. GB1220442.6, dated Apr. 16, 2013, pp. 1-4.
Patent Cooperation Treaty, PCT, Notification of Transmittal of the International Search Report and the Written Opinion of the International Searching Authority, or the Declaration, Applicant's File Reference GB120132, International application No. PCT/EP2013/065898, dated Oct. 14, 2013, pp. 1-10.
"TN-29-42: Wear-Leveling Techniques in NAND Flash Devices", Micron®, pp. 1-8, © 2008 Micron Technology, Inc.
MICRON, "Wear-Leveling Techniques in NAND Flash Devices The Importance of Wear Leveling", TN-29-42, 2008, p. 1-8, Micron Technology, Inc.
Palmer et al., "Fast Data Back-Up and Restore Between Volatile and Flash Memory", Filed on Aug. 19, 2003, p. 1-52, GB Patent Application No. 1314810.1.
UK Intellectual Property Office, "Examination Report under Section 17/(5)", dated Jan. 27, 2014, International Application No. GB 1314810.1.
Palmer et al., "Back-Up and Restoration of Data Between Volatile and Flash Memory", UK Patent Application No. 1220442.6, filed on Nov. 14, 2012, pp. 1-29.
Borland, Jes, "Improving the Performance of Backups", Brent Ozar Unlimited®, © 2015, Jan. 21, 2014, <http://www.brentozar.com/archive/2014/01/improving-the-performance-of-backups/>, pp. 1-7.
Appendix P, list of patents and patent applications to be treated as related, Feb. 13, 2017, 2 pages.
Palmer et al., "Back-Up and Restoration of Data Between Volatile and Flash Memory", U.S. Appl. No. 14/822,140, filed Aug. 10, 2015, 51 pages.
"Patent Act 1977: Search Report under Section 17 and 18 (3)", Intellectual Property Office, Application No. GB1612055.2, dated Dec. 14, 2016, 6 pages.

* cited by examiner

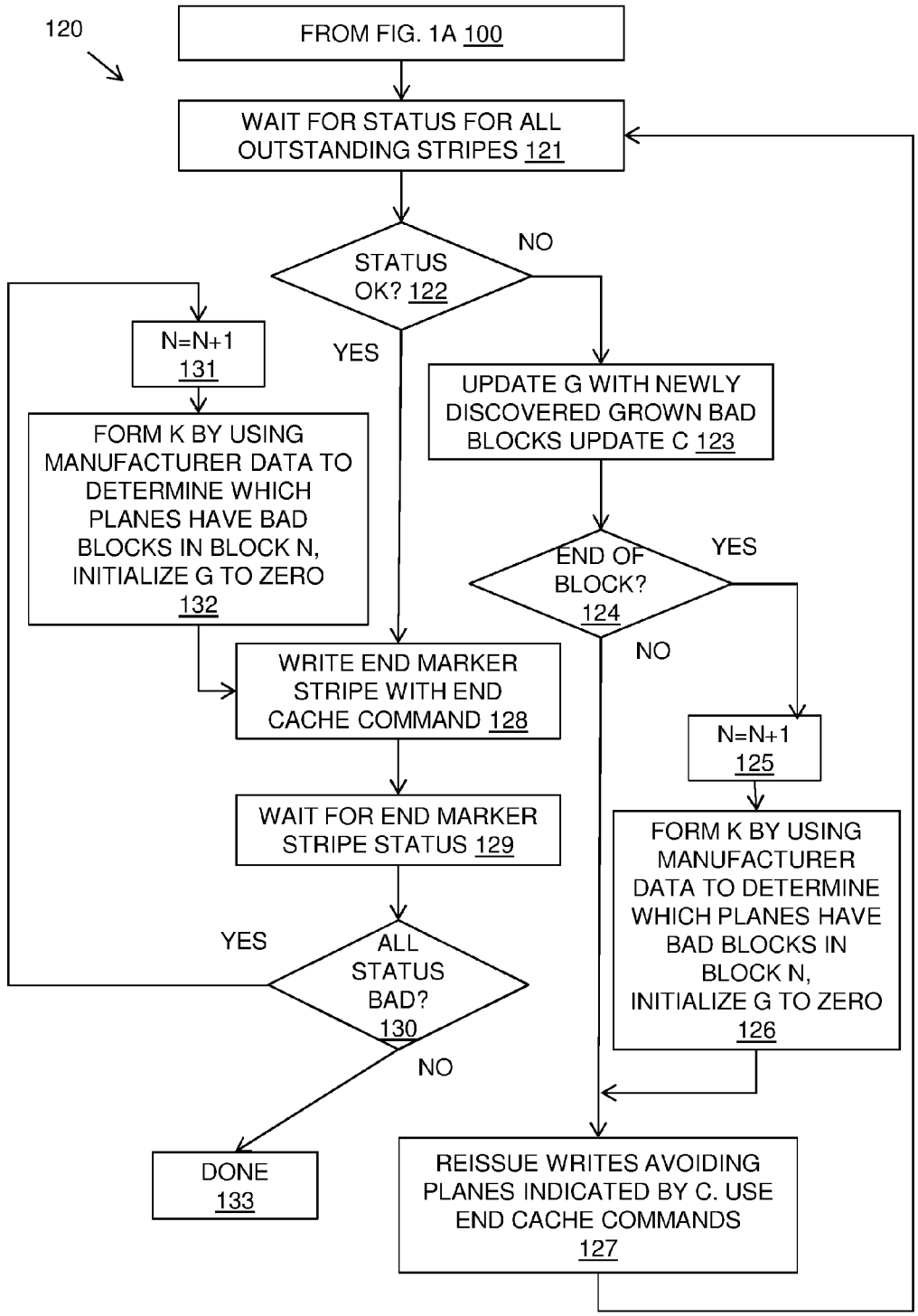

BACK-UP AND RESTORATION OF DATA BETWEEN VOLATILE AND FLASH MEMORY

BACKGROUND OF THE INVENTION

The present invention relates to the field of data back-up and restoration, and more specifically, to back-up and restoration of data between volatile and flash memory.

When a main power fail is detected in a system, a pre-charged standby capacitor acts as a temporary power supply so that a controller device can copy data from volatile system memory into flash memory, thereby preserving it. On the resumption of main power, the backed up data can then be read from flash memory and restored back into the volatile memory. There is limited energy and therefore limited time to perform the back-up, so a method to improve performance is required.

Current back-up solutions deal with the main failure mode of flash devices which is the wearing out of blocks after many (~3,000) erase/program cycles. Current solutions mitigate this by using wear-leveling algorithms that determine which blocks have been the most used and which will have a high level of wear, these most used blocks are then avoided. Despite the use of wear-leveling, this does not eliminate the possibility of encountering an unexpected page program error during the back-up. When such a "Grown Bad Block" is encountered, current solutions have no other recourse than to erase a fresh flash block in order to compensate for space lost. Erasure takes significant time and hence detriments the rate at which data can be backed up.

Wearing out of blocks is of particular concern in NAND flash technology, although this may also be of concern in NOR flash technology.

SUMMARY

According to a first aspect of the present invention there is provided a method for controlling back-up of data to flash memory, comprising: organizing back-up data into stripes, wherein a stripe is a set of pages across all available flash memory devices, dies and planes which have the same block and page address; maintaining metadata indicating locations of known bad planes and grown bad planes; using the metadata when writing back-up data to determine which planes to send cache program commands to; and sending cache program commands to three or more stripes of data simultaneously including providing an indication in a stripe that the stripe is handling a cache program command; wherein if a grown bad block is encountered whilst saving a stripe of data, the stripe of data is re-written to the next available page address avoiding the grown bad block.

The method provides the advantage of enhancing the performance of the back-up method to take advantage of cache commands whilst maintaining dynamic adjustment to the presence of grown bad blocks as they are discovered during the saving of data to flash memory.

Providing an indication in a stripe being written that the stripe is handling a cache program command may include setting a bit in metadata indicating that the following page in the plane will also be programmed Maintaining metadata may include maintaining a combined bad plane register of known bad planes and grown bad planes, wherein the combined bad plane register carries out an OR operation of the known bad planes and the grown bad planes. This has the benefit that a single metadata map may be read.

For each plane, a cache register may allow a host to move data in or out of flash memory whilst the flash memory is busy carrying out an array operation.

Sending cache program commands to three or more stripes of data simultaneously may include allowing a host to transfer data for a second page program whilst a plane is busy completing the previous page program.

The method may include for each stripe determining if any pages have failed; if no pages have failed in a stripe, continue writing next stripe; if one or more pages have failed in a stripe, update the grown bad plane metadata for the three or more stripes, end a cache program in next stripe, and re-write the previous three or more stripes.

Maintaining metadata indicating locations of known bad planes and grown bad planes may include a known bad plane register, a grown bad plane register, and a combined register of all bad planes.

The method may include embedding bad block metadata in the backed-up data for use during restoration. The method may further include restoring backed-up data from flash memory including reading metadata from a stripe of backed-up data, and issuing cache read commands for planes for which the metadata is good. Restoring backed-up data from flash memory may include updating the metadata in the form of known bad planes and grown bad planes from metadata embedded in the backed-up data in the flash memory.

By improving the performance of the back-up operation, more data is saved to flash memory in a given amount of time. This means that smaller capacitors or batteries may be needed to hold the system power up whilst the back-up is taking place which in turn drives down the overall cost of the system.

Furthermore, if the size of stripe is matched properly to the bandwidth of the flash interface being used, the method described can improve the performance dramatically.

According to a second aspect of the present invention there is provided a system for controlling back-up of data to flash memory, wherein the system includes a back-up engine having a processor for backing-up data to flash memory formed of multiple flash devices, wherein the back-up engine provides commands to multiple flash device controllers having dedicated flash interfaces to the multiple flash devices, the back-up engine comprising: a data structure component for organizing back-up data into stripes, wherein a stripe is a set of pages across all available flash memory devices, dies and planes which have the same block and page address; a volatile storage for storing metadata regarding the back-up process including: maintaining metadata indicating locations of known bad planes and grown bad planes, wherein the volatile storage has a temporary power supply; a back-up writing component using the metadata when writing back-up data to determine which planes to send cache program commands to; and a caching component for sending cache program commands to three or more stripes of data simultaneously including providing an indication in a stripe that the stripe is handling a cache program command; and a re-writing component, wherein if a grown bad block is encountered whilst saving a stripe of data, the stripe of data is re-written to the next available page address avoiding the grown bad block.

The caching component may include providing an indication in a stripe being written that the stripe is handling a cache program command and setting a bit in metadata indicating that the following page in the plane will also be programmed.

The volatile storage for storing metadata may include a combined bad plane register of known bad planes and grown bad planes, wherein the combined bad plane register carries out an OR operation of the known bad planes and the grown bad planes.

The caching component may include, for each plane, a cache register allowing a host to move data in or out of flash memory whilst the flash memory is busy carrying out an array operation.

The caching component configured to send cache program commands to three or more stripes of data simultaneously may include allowing a host to transfer data for a second page program whilst a plane is busy completing the previous page program.

The re-write component for each stripe may determine if any pages have failed; if no pages have failed in a stripe, the write component continues writing next stripe; if one or more pages have failed in a stripe, the re-write component may update the grown bad plane metadata for three or more stripes, end a cache program in next stripe, and re-write the previous three or more stripes.

The volatile storage for storing metadata indicating locations of known bad planes and grown bad planes may include a known bad plane register, a grown bad plane register, and a combined register of all bad planes.

The system may include a metadata embedding component for embedding bad block metadata in the backed-up data for use during restoration.

The system may further include a restoring component for restoring backed-up data from flash memory including reading metadata from a stripe of backed-up data, issuing cache read commands for planes for which the metadata is good. The restoring component may include updating the volatile storage to store the metadata read from the backed-up data including locations of known bad planes and grown bad planes.

According to a third aspect of the present invention there is provided a computer program product controlling back-up of data to flash memory, the computer program product comprising a computer readable storage medium having program instructions embodied therewith, the program instructions executable by a processor to cause the processor to: organize back-up data into stripes, wherein a stripe is a set of pages across all available flash memory devices, dies and planes which have the same block and page address; maintain metadata indicating locations of known bad planes and grown bad planes; use the metadata when writing back-up data to determine which planes to send cache program commands to; and send cache program commands to three or more stripes of data simultaneously including providing an indication in a stripe that the stripe is handling a cache program command; wherein if a grown bad block is encountered whilst saving a stripe of data, the stripe of data is re-written to the next available page address avoiding the grown bad block.

BRIEF DESCRIPTION OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings.

Preferred embodiments of the present invention will now be described, by way of example only, with reference to the following drawings in which:

FIG. 1B is a flow diagram of an extension of the first example embodiment of FIG. 1A;

Figure 1A:
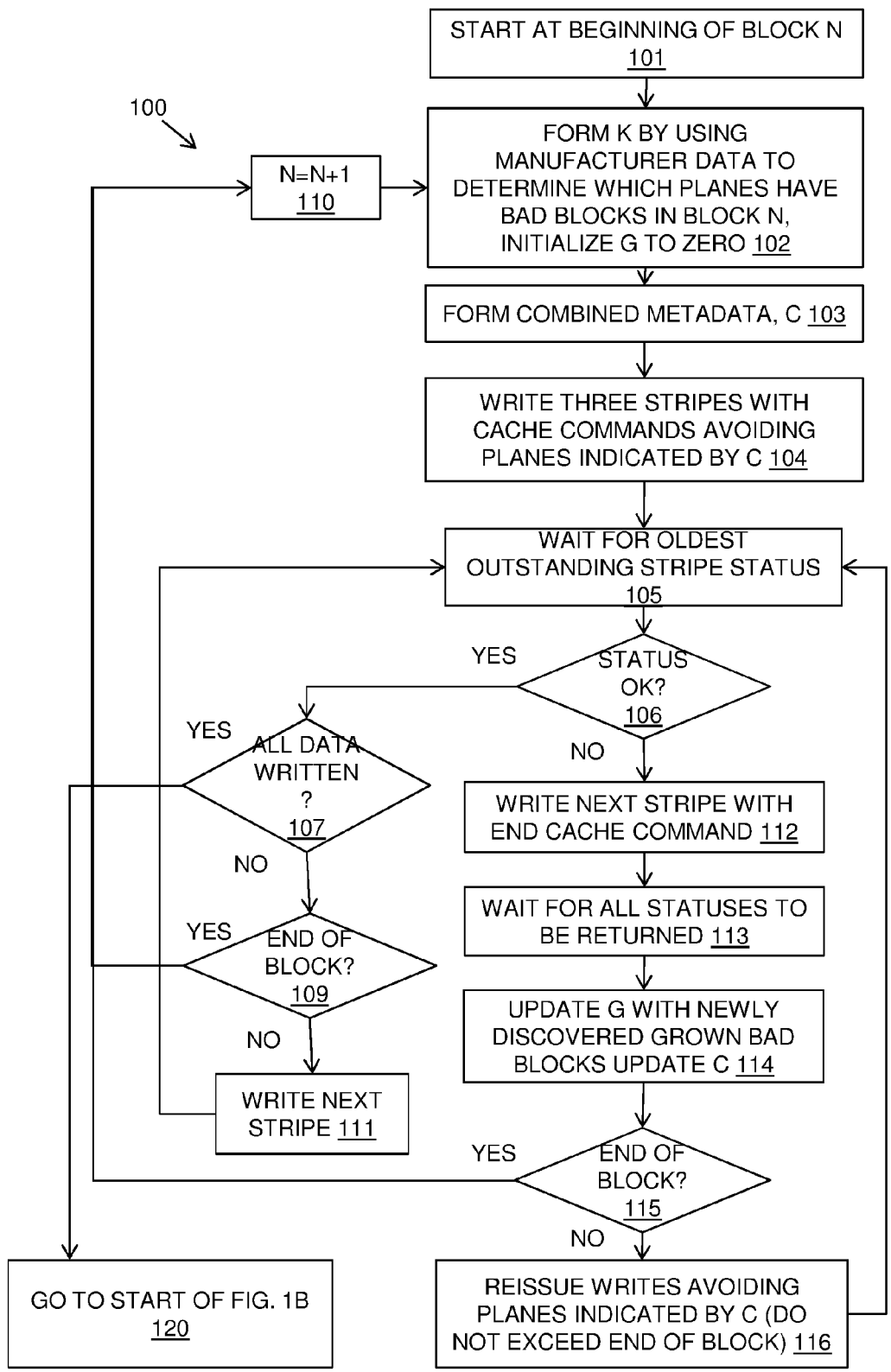
FIG. 1A is a flow diagram of a first example embodiment of a method in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

DETAILED DESCRIPTION

Method and system are provided for backing up data from a volatile memory source (e.g. DRAM) to non-volatile flash memory and restoring it back to volatile memory. The described method and system may be applied to both NAND and NOR flash memory, in particular where wear-out is of concern.

The described method saves data to flash memory just prior to a system power loss and allows it to be restored once power returns. The method is adaptive because it can deal with defects within the flash memory that were unknown to exist prior to starting the save. Defects may prevent data being saved to certain blocks due to excessive wear. These previously unknown defective blocks are referred to as "grown bad blocks" and cannot be detected until an attempt to write to them is made. Upon detecting a grown bad block, the method uses features to ensure that the data can still be successfully saved and later restored.

The method uses the concept of organizing backed-up data into stripes. Flash devices consist of multiple dies which in turn consist of two or four planes. Each plane is further sub-divided into blocks which in turn are divided into pages. A stripe is a set of pages across all available flash devices, dies and planes which have the same block and page address. If the method comes across a grown bad block whilst saving a stripe of data it will re-write that stripe at the next available page address avoiding the defective block.

The method also embeds metadata along with the backed-up data. This metadata may consist of bitmaps indicating the locations of previously known bad blocks and newly discovered grown bad blocks. The metadata may also consists of a stripe number starting at 0 for the first stripe and incrementing with every stripe and a length field indicating the amount of data saved. The metadata may be written into every page of a stripe. At the end of the saved data image, the method may write an end marker that is a stripe whose length field is zero. The method may then use the metadata to successfully re-construct the data during a restore according to the description given below.

When a flash system is programming or reading from a page, it is known as an array operation. In such operations, a plane is equipped with a page register that is used as a buffer between the target page in the memory array and the host. For example, for a page program the host shifts write data into the page register before issuing a program command instructing the flash system to move the write data into the target page.

In the described method and system, each plane may also be equipped with a cache register. These registers improve performance by allowing the host to move data in or out of the flash system whilst the flash system is busy performing an array operation.

Particularly useful is the cache program command. Once the host has transferred data into the flash system for a first program command, it can issue a cache program command. This enables the host to immediately begin transferring data for another page in the same plane (by writing it into the cache register) whilst the flash system is busy programming the page for the previous program command.

It can take approximately 1.5 to 2 ms to program a page. If a normal page program command is used, the host cannot transfer data to program another page in the same plane during this busy time. This means that bandwidth can be lost whilst waiting for the plane to become ready again to accept data. A cache program command allows the host to transfer data for a second page program whilst the plane is busy completing the previous page program thereby making use of the available bandwidth that the flash-host interface provides and in turn making a performance improvement.

An embodiment of a method for back-up of data is described. A non-volatile memory system, for example, in the form of a NAND or NOR flash memory system is provided for back-up for volatile memory. Sufficient blocks of data may be pre-erased (before the back-up mechanism is enabled) from the flash memory system to hold the amount of data to be backed-up. A number of spare blocks may also be pre-erased.

A set of registers may hold the starting location of where to write the back-up data to flash memory, the starting location of where to start reading from in source memory as well as the amount of data to back up. These registers may be initialized before the back-up operation by the user.

A power failure may occur and a temporary power source may be activated such as a charged capacitor during which a back-up process may be carried out.

A back-up process may commence by backing up data to blocks of the flash memory system in stripes as described in detail below.

During the back-up process, two scenarios may be encountered. Firstly, there may be known bad blocks that cannot be written to. Secondly, there may be newly encountered (grown bad) corrupted blocks that cannot be written to of which there is no information prior to the back-up process.

If a known bad block is encountered, the data is written to the next page in the stripe. The page of the bad block may be avoided in every subsequent stripe of the block. Metadata regarding the stripe size is maintained to indicate the shorter size due to the bad block.

If a grown bad block is encountered which was not known about previously, an error may be received indicating the bad block. The stripe may be re-written at a next available set of pages avoiding the page of the bad block. The page of the bad block may be avoided for all subsequently written stripes for the block.

Metadata at a back-up engine may be maintained regarding known bad planes (K), grown bad planes (G) and combined bad planes (C). The metadata indicates where the bad blocks are. The bitmaps in the metadata may refer to which planes have bad blocks at the block address where the metadata is saved. There is one bit in each bit map to represent a single plane.

As mentioned, planes are divided into blocks which are further divided into pages. Suppose data is being saved at block address 0. The metadata saved in the pages of block 0 may indicate which planes contained bad blocks whose block address was 0. So when the metadata is read back during a restore operation, if it is read back from a page in block 0 then it tells us there is a bad block at block address 0 at a specific plane. Similarly, if metadata is read from a page in block 1 then it indicates that a specific plane contains a bad block at block address 1.

The term "bad planes" is used to indicate planes to avoid for the current block address or Logical Block Address (LBA). At the next LBA, the same planes may have each have a good block.

Referring to FIG. 1A, a flow diagram 100 shows an example embodiment of the aspect of back-up of data of the described method.

A back-up method may start at the beginning of a block n 101. The known bad planes metadata K may be formed 102 by using manufacturer data to determine which planes have bad blocks in block n. The grown bad planes metadata G is initialized to zero. Combined metadata C indicating all bad planes (whether known or grown bad) may be formed 103.

This combined metadata C may be checked for the planes of a stripe prior to writing a stripe. It may be determined if any of the planes are bad. If so, a next set of blocks may be checked.

When a good set of planes is found, three or more stripes may be written 104 with cache program commands avoiding planes indicated in the combined metadata C. An indication that the writes are cache program commands is provided in the back-up engine metadata. Caching may be carried out with four or more stripes; however, this requires re-write of more stripes if there is an error with the oldest one.

The method may wait 105 for the oldest stripe status to return. The method may determine 106 if the status for the oldest stripe is good.

If the status returns all planes are good, it may be determined 107 if all the data has been saved. If all data has all been saved, the method may proceed as shown in the flow diagram 120 of FIG. 1B.

If it is determined 107 that not all the data has been saved, it may be determined 109 if it is the end of the block. If it is the end of the block, the method loops to operation 102 and increments n 110. If it is not the end of the block, the next stripe may be written 111 with a cache command and the method loops to operation 105 to wait for the oldest outstanding stripe status.

If it is determined at operation 106, that the status of the oldest outstanding stripe is not good, a next stripe may be written 112 with an end cache command. The method may then wait 113 for all statuses to be returned. The grown bad planes metadata G may be updated 114 with the newly discovered grown bad blocks and the combined metadata C may also be updated.

It may then be determined 115 if it is the end of the block. If it is then the method may loop to operation 102 and increment n 110. If it is not the end of the block, the writes are reissued 116 avoiding the planes indicated by the combined metadata C 116 without exceeding the end of the block.

As the back-up proceeds the method may embed metadata, about newly encountered corrupt blocks, along with the data to be saved within the flash back up image. Providing sufficient spare blocks have been pre-erased, the method may continue backing up the data despite encountering unexpected flash page programming errors and without having to spend "capacitor" time erasing new blocks as a result. The dump may continue even if the failure of a whole flash device is experienced. The method may even tolerate the failure of multiple devices provided at least one remains usable.

Referring to FIG. 1B, a flow diagram 120 shows an example embodiment of a further aspect of back-up of data of the described method. Once the back-up engine has decided that all data has been written, before it writes an end marker, it must wait for the last two data stripes (n–2 and n–1) to complete. If grown bad blocks are encountered whilst writing those last two stripes then they may be re-written as needed.

The method may wait 121 for the statuses for all outstanding stripes. It may be determined 122 if all the statuses are good.

If they are not all good, the grown bad plane metadata (G) may be updated 123 with the newly discovered grown bad blocks, and the combined metadata (C) may also be updated. It may be determined 124 if it is the end of the block. If so, the block is incremented 125 and the known bad plane metadata (K) may be formed 126 by using manufacturer data to determine which planes have bad blocks in the new block N, and the grown bad planes metadata (G) may be initialed to zero. If it is not the end of the block, or the above operations 125, 126 have been taken, then the method may reissue 127 the writes avoiding planes indicated by the combined metadata (C), using cache commands. The method may then loop to wait 121 for all the statuses to return.

If at operation 122 it is determined that the statuses are all good, then an end marker stripe may be written 128 with an end cache command. The method may then wait 129 for the end marker stripe status.

It may be determined 130 if the status is bad. If the status is not bad, the method ends 133. However, if the status is bad, the method may increment 131 the block and the known bad planes metadata (K) may be formed 132 by using manufacturer data to determine which planes have bad blocks in the new block N, and the grown bad planes metadata (G) may be initialed to zero. The end marker stripe may then be written 128 to the new block.

Figure 2:
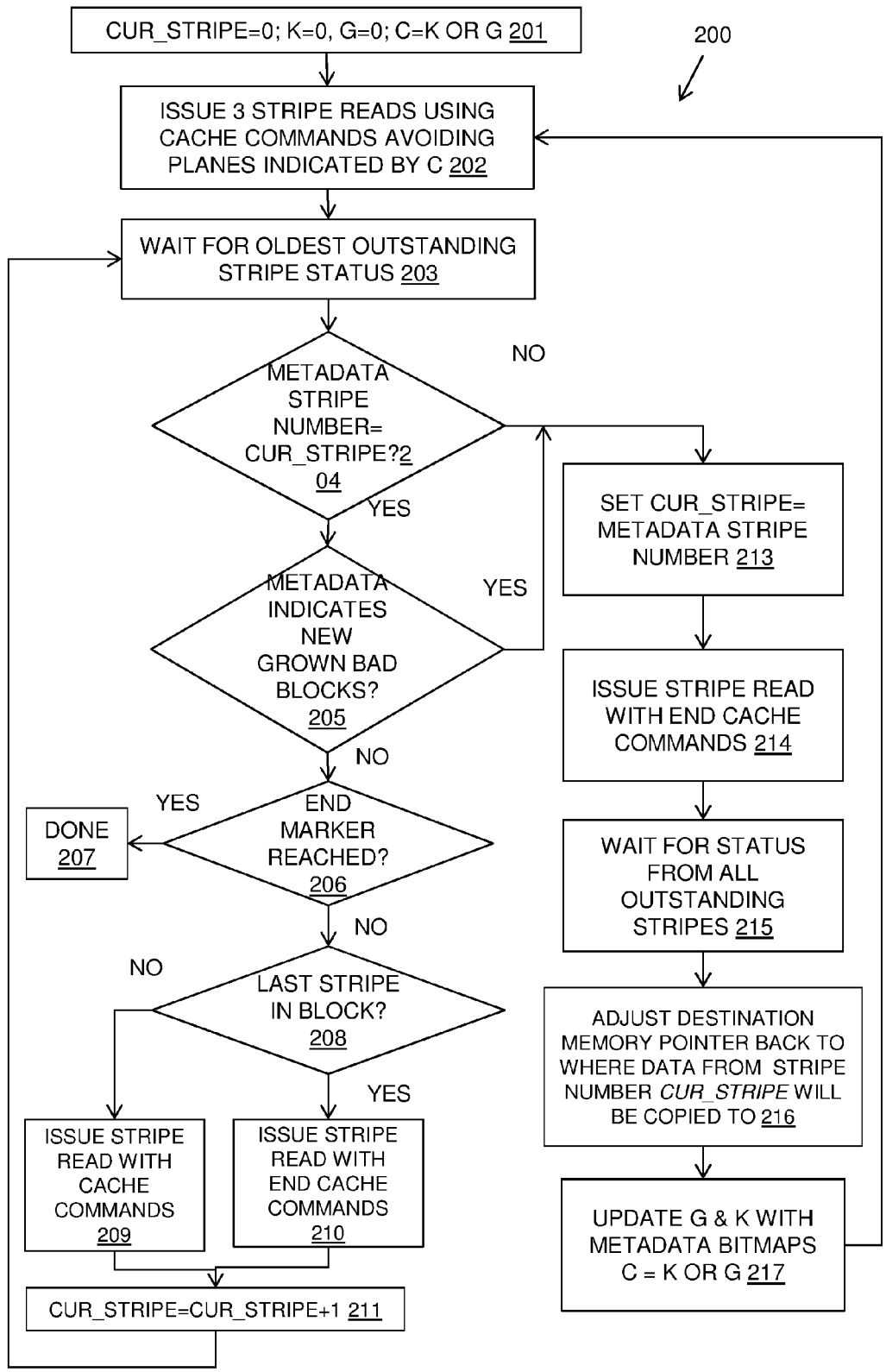
FIG. 2 is a flow diagram of a second example embodiment of a method in accordance with the present invention.

Referring to FIG. 2, a flow diagram 200 shows an example embodiment of an aspect of restoration of data of the described method.

Current stripe (Cur_Stripe), known bad planes metadata (K) and grown bad planes metadata (G) may be variables stored in the back-up engine when it is doing the restore. K and G may be updated as metadata from the stored back-up is read. The variables may be initialized with Cur_Stripe as zero, with no known bad planes (K=0) and no grown bad planes (G=0).

When the backed up data is to be restored to a target memory, three or more stripe reads may be issued 202 using cache commands and avoiding planes indicated by the combined bad planes metadata C. The method may then wait 203 for the oldest outstanding stripe status.

When the oldest outstanding stripe status returns, it may be determined if the metadata stripe number is equal to the current stripe. If it is, it may be determined 205 if the metadata indicates and new grown bad blocks. If the answer is no, it may be determined 206 if an end marker has been reached. If an end marker has been reached the method ends 207.

If an end marker has not been reached, it may be determined 208 if the stripe is the last stripe in the block. If it is not the last stripe in the block, a next stripe read may be issued 209 with a cache command. If it is the last stripe in the block, a next stripe read may be issued 210 with an end cache command. In both cases, the current stripe number may be incremented 211 and the method may loop to operation 203 to wait for the oldest stripe status to return.

If the metadata stripe number does not equal the current stripe at operation 204, or the metadata indicates new grown bad blocks at operation 205, the current stripe may be set 213 to the metadata stripe number. A stripe read may be issued 214 with an end cache command. All statuses may be waited for 215 from all outstanding stripes. The destination memory pointer may be adjusted 216 back from where the data from the stripe number may be copied to. Metadata may be updated 217 for grown bad planes, known bad planes and combined bad planes from the metadata read from the stored back-up. The method may then loop to operation 202 to issue three stripe reads.

The metadata may be used to determine the locations of any known bad blocks and/or any new corrupted blocks or whether an entire device failed. From this, the method may determine how to correctly restore the data despite these set backs. In this way, the method adapts to errors encountered during a back-up.

Flash devices are divided into dies and each die may have two or four planes. In the embodiments described it is assumed that two planes per die flash devices are used. The described method and system may easily be adapted for four planes per die devices. Each plane may consist of a certain number of blocks (usually multiples of 1024) and each block may have a certain number of pages (usually multiples of 128). Each page may hold a given payload of data (typical sizes are multiples of 8 KB). It is possible to control multiple flash devices simultaneously through separate interfaces as shown in FIGS. 3A and 3B below.

Figure 3A:
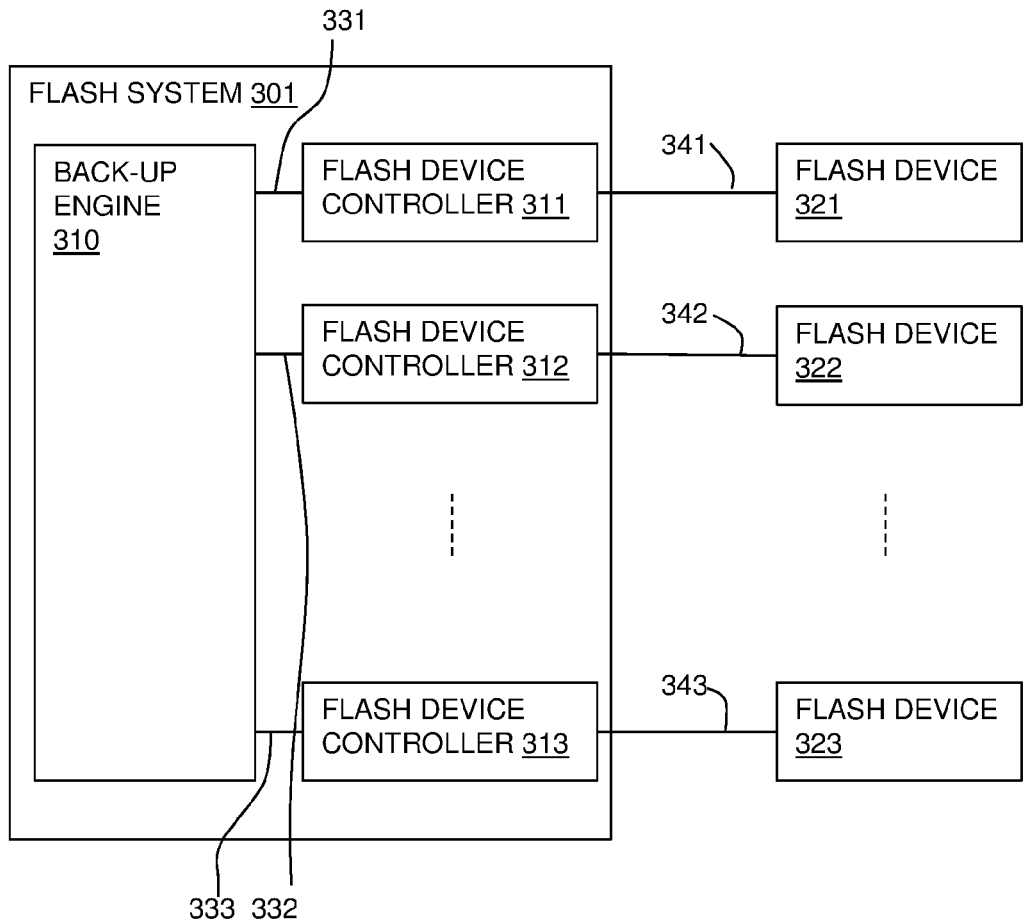
FIGS. 3A and 3B are block diagrams of an example embodiment of a system in accordance with the present invention.
Figure 3B:
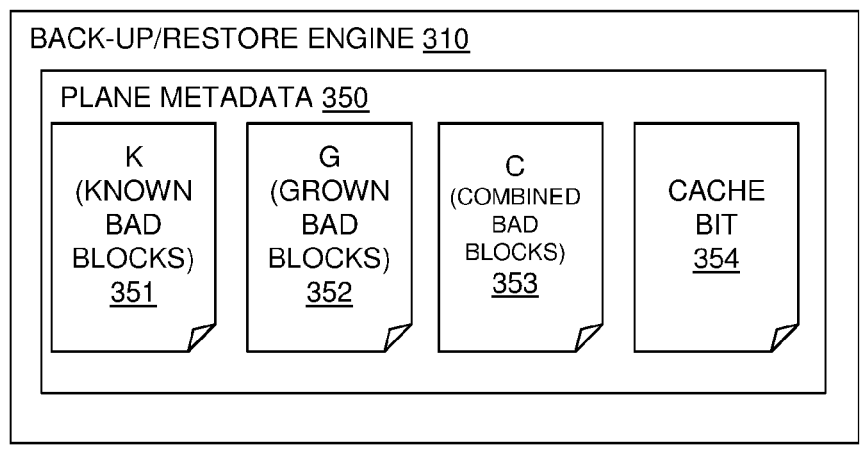

FIGS. 3A and 3B are block diagrams of an example embodiment of a flash system 301. The flash system 301 is sub-divided into discrete flash device controllers 311, 312, 313 and a back-up engine 310. Each flash device controller 311, 312, 313 controls a flash device 321, 322, 323 on a particular channel 341, 342, 343.

The back-up engine 310 hereinafter referred to as a back-up engine 310 issues discrete commands to each flash device controller 311, 312, 313 instructing them to back-up a portion of system data to a flash page. The discrete commands are issued on a command bus 331, 332, 333 between the back-up engine 310 and each flash device controller 311, 312, 313 as shown in FIG. 3.

The back-up engine 310 keeps metadata 350 for a plane of both a known bad plane register 351 and a grown bad plane register 352 in two separate registers within the engine 310. The registers may be maintained as bitmaps and may be referred to as K (for known) and G (for grown). These registers are volatile so the data may be lost once power fails.

The back up engine 310 may be saving data at a particular block address. Once it has filled up all the available pages within that block on all available planes then it may add one to the block address to move to the next block. So the known bad plane register 351 and grown bad plane register 352 indicate for the block address the engine is currently working on, which planes contain known or grown bad blocks. The phrase "bad plane" really means that that plane has a bad block at the current block address.

At the next block address the same plane might have a good block, which is why K and G may be initialized to all zeroes whenever the engine starts at the beginning of a block. K is initialized to zero and then information provided by the manufacturer may be used to work out whether any planes have known bad blocks at the current block address. G is initialized to zero and as pages are written in the new block, some planes may return errors which indicate that those planes have grown bad blocks at the current block address.

The back-up engine 310 also stores the current value of these bitmaps into every flash page of a stripe along with the data it backs-up. Thus, when the restore of the data happens, the engine can re-construct where the bad blocks were by reading the metadata in the non-volatile flash pages.

The flash manufacturer provides a list of the bad blocks it discovered at the time the device was produced so the engine can immediately update K with the positions of known planes, which have bad blocks at the current block address. As the back-up proceeds and new bad blocks are discovered, G may be updated on the fly.

During the back-up operation, registers K and G are initialized to all zeroes whenever the engine 310 starts at the beginning of a block, i.e. no bad planes encountered thus far within that block address. Since G is all zero there is no prior knowledge of grown bad blocks.

The back-up engine 310 may also maintain a combined plane register 353, C. The value of the combined plane register, C is the logical OR of K and G. Therefore any change to G in turn updates the value of C on the fly.

The back-up engine 310 may also maintain a cache bit register 354 to keep track of blocks that have been written as a cache program command.

The described method and system as described in FIGS. 1A, 1B and 2 and as further described below may be implemented in the back-up engine 310.

The described method uses a concept of a stripe, which consists of all the pages in every available plane and in every available channel that have the same page address and block address.

Figure 4:
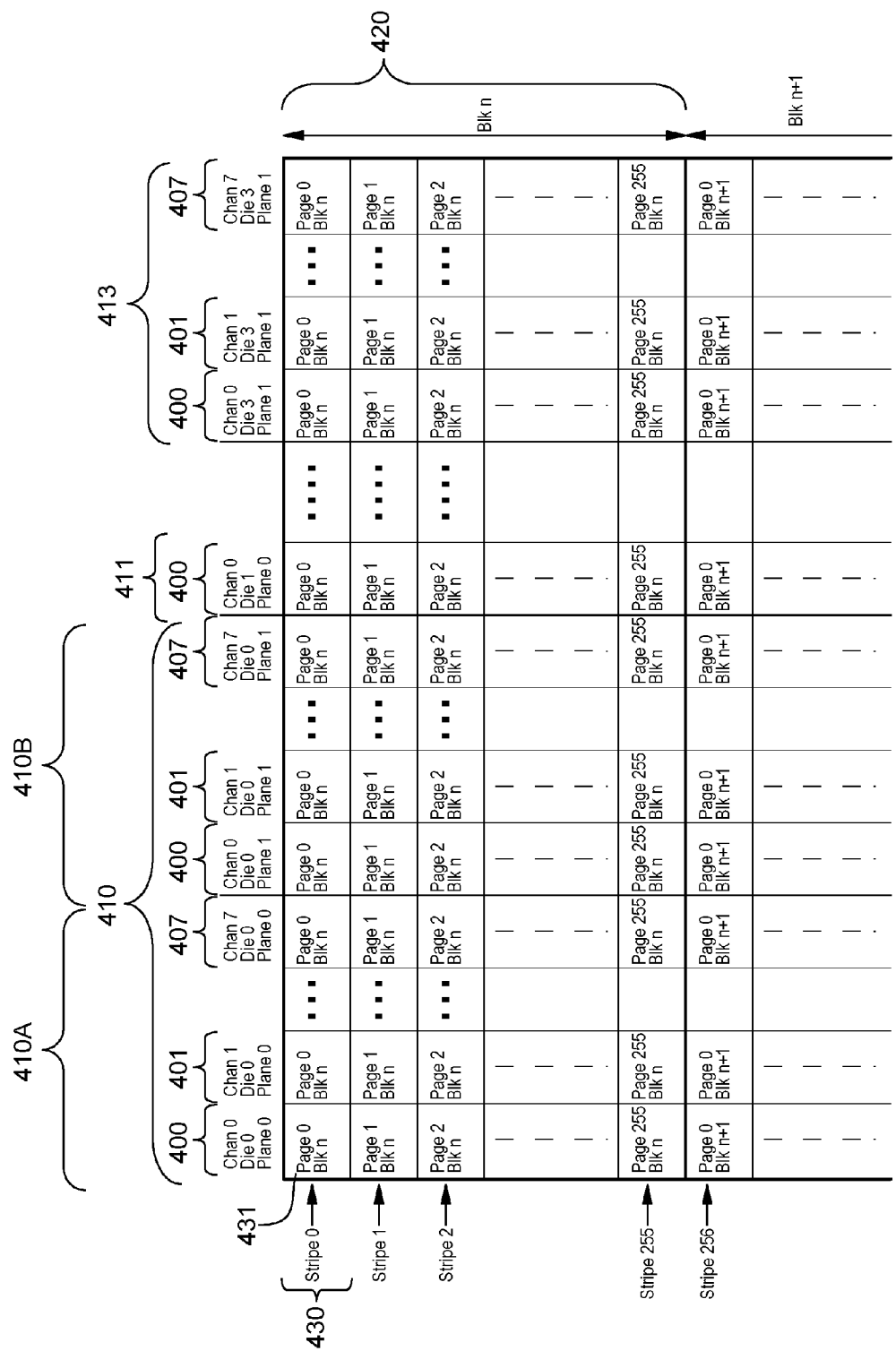
FIG. 4 is a schematic diagram of an example embodiment of a flash memory system in accordance with the present invention.

Referring to FIG. 4, a schematic diagram 400 shows an example embodiment of several stripes that reside at various page and block addresses in a flash memory system.

In this example embodiment, there are eight active channels 400-407 (numbered 0 to 7) with each channel containing four dies 410-413 (numbered 0 to 3). Given that there are two planes 410A, 410B per die, a single stripe consists of 64 pages. In addition, each block 420 on a plane consists of 256 pages. Thus across all channels, dies and planes, there can be 256 stripes 430 (0 to 255) per logical block address (LBA).

Each stripe 430 is a set of pages 431 across all available flash devices which has the same block and page address across all the channels, dies and planes.

A back-up process using the example embodiment of FIG. 4. It is assumed that the data to be backed up to flash memory (the source data) exists in a contiguous memory space within the system.

Back-up begins by copying enough source data to fill 64 flash pages in Stripe 0 430, then doing the same for Stripe 1, 431 and so on until all the required data has been backed up.

When this occurs, an end marker stripe is written at the next available page address (at page x+1, block n).

When power is restored, the saved data in flash memory can be copied back into a target location in system memory. This data restore begins by reading the flash data from Stripe 0 and writing it to this target location. The data from Stripe 1 is then read and copied to the next part of target space and so on. The restore operation finishes when the end marker is read.

In order to adapt to errors during the back-up process and in order to log the locations of flash blocks that have become bad or unusable, the described method writes a set of metadata into each page of each stripe (the remainder of a page may be filled up with source data). The metadata consists of the following.

Stripe number—beginning from 0 and usually increments with each stripe. However, newly discovered bad blocks can cause page program errors. When these are encountered, the method may have to back track a little and re-write stripes at a later location. Thus, it is possible for a flash image to contain two or more stripes which have the same Stripe number. (Note that it is not possible to overwrite a piece of flash memory once it has been written without performing a complete erase of a block. A stripe re-write must therefore be done on a "fresh" piece of flash memory).

Stripe Size—This is the amount of backed up data contained within the stripe. The end marker is denoted by this field being zero.

Known Bad Plane Register—This may also be a bitmap which has one bit to represent every plane in the stripe. If a bit is on, it indicates that the corresponding plane contains a bad block at the block address where the metadata is saved and that this block was known to be bad before the back up operation began. Manufacturers provide a list for each flash device sold indicating the locations of each block known to be unusable within the device.

Grown Bad Plane Register—This may also be also a bitmap which has one bit to represent every plane in the stripe. If a bit is on, it indicates that the corresponding plane has a bad block at the block address where the metadata is saved. This block was not included in in the original bad block list provided by the flash manufacturer.

As a dump operation proceeds within a particular LBA, the back-up engine keeps two bitmaps: a known bad plane register and a grown bad plane register. The known bad plane register indicates the planes which have a block known to be bad at the current LBA prior to the initiation of the dump operation. The grown bad plane register indicates the planes which have a block previously unknown to be bad, prior to the initiation of the dump operation and discovered to be bad as the dump operation proceeded. Each plane in all available flash devices is represented by one bit in each of these bitmaps. A "1b" indicates the plane belongs to a bad block (either known or grown) whilst "0b" indicates the plane belongs to a usable block. Thus for the example of FIG. 4, each map contains 64 bits.

The method uses these bitmaps to determine which planes to send cache program commands to by firstly ORing the current versions of the known bad plane register and grown bad plane register together to form a combined bad plane register, C.

The described method writes at least three stripes at once rather than two in order to efficiently use the time provided by the pre-charged standby capacitor. To each and every plane n (0<=n<64) where C(n)=0b the back-up engine may have three program commands (one for each stripe) outstanding.

Note that all the program commands for one stripe are sent before the program commands for the next stripe are sent. It may also set a bit (called "cache") for each of these commands. When "1b", the cache bit indicates to the Flash Device Controllers that it is safe to use a cache program command (rather than a normal program command) to program the page. By setting the cache bit to "1b", method is promising that the following page in the plane will also be programmed Flash protocol (e.g. ONFI or Toggle 2) stipulates that a cache command may only be used to program a page if there will be a following page in the same plane to be programmed immediately after.

Figure 5A:
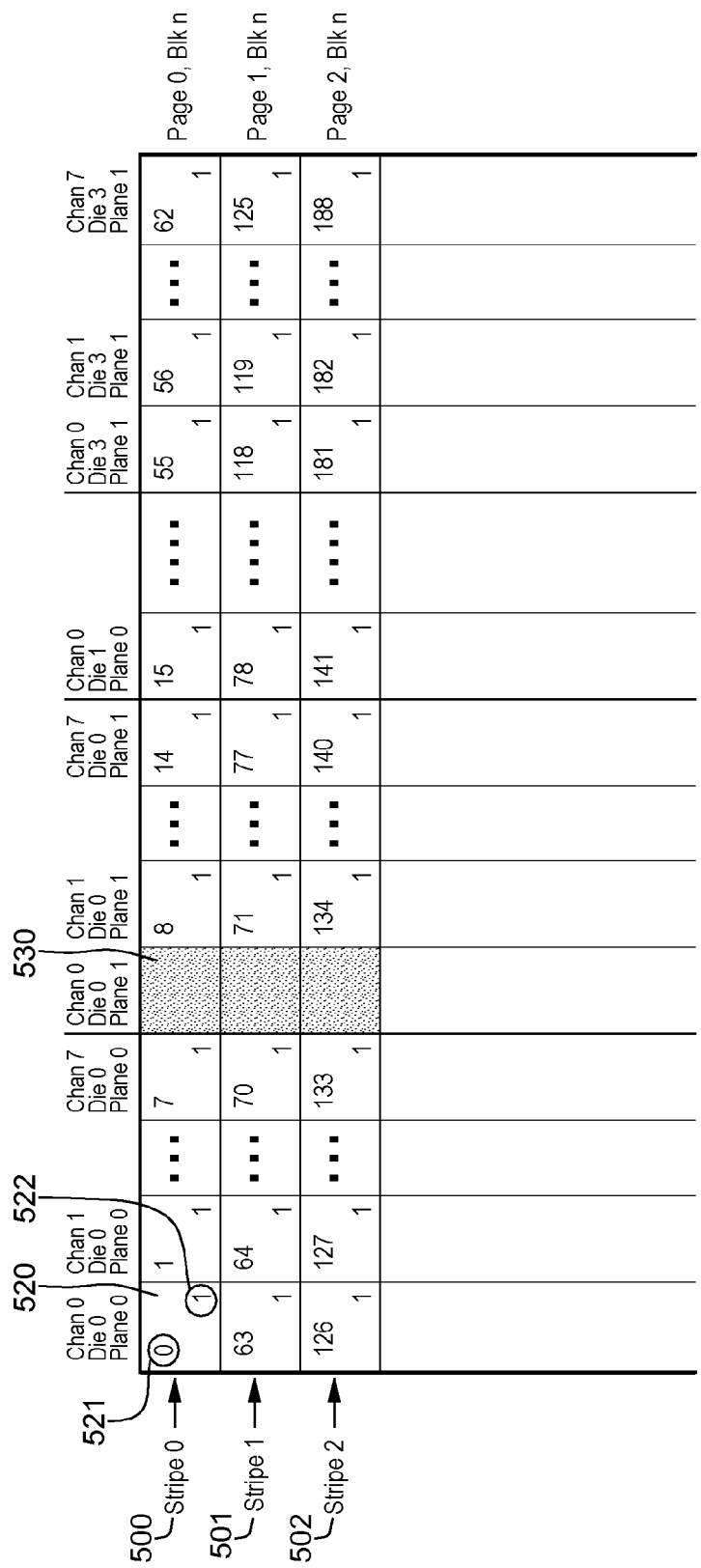
FIGS. 5A-5C are schematic diagrams of an example embodiment of stages of a back-up write in accordance with the present invention.
Figure 5B:
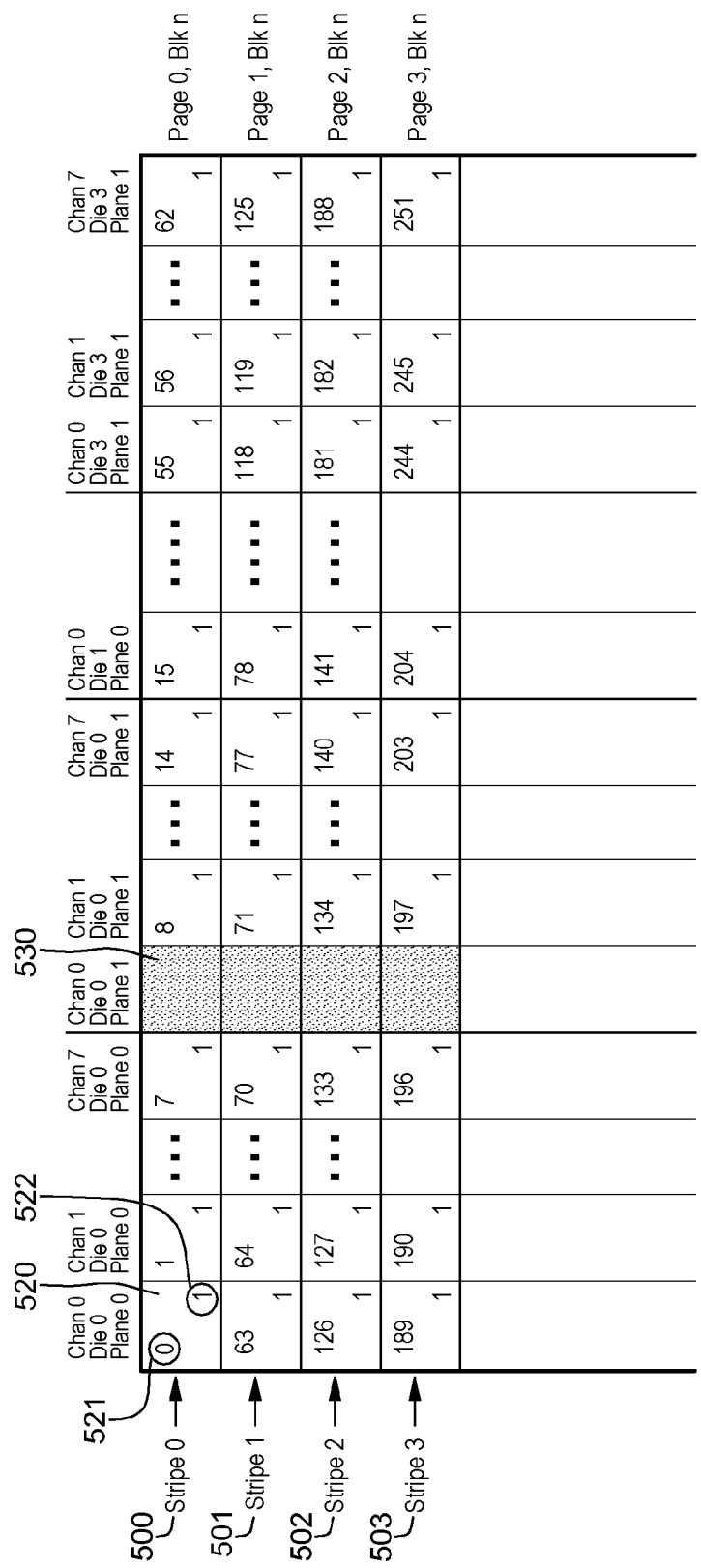
Figure 5C:
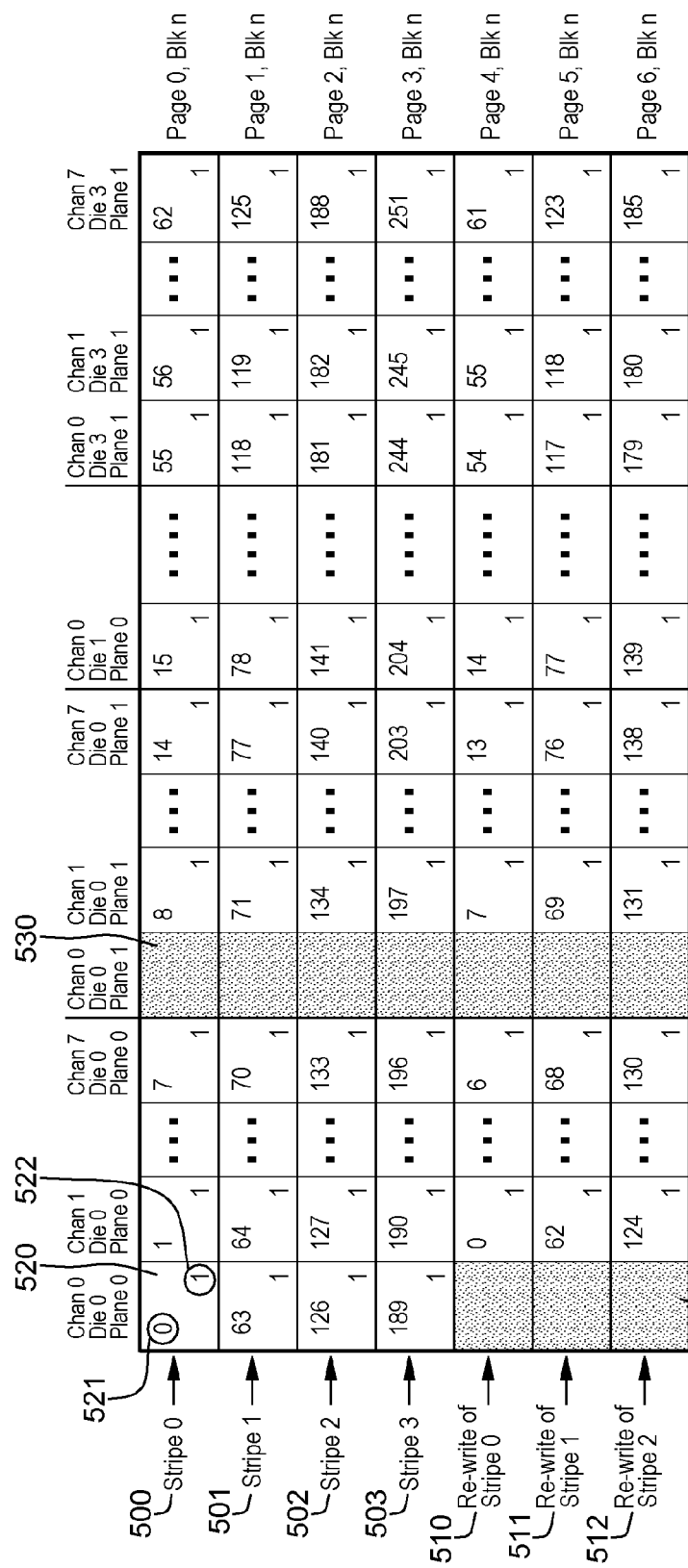

In the example shown in the schematic diagrams of FIGS. 5A, 5B and 5C, the back-up engine sends commands to write stripes 0, 1 and 2 500, 501, 502. A page of source data is denoted by the ascending numbers 521 in the top left of each box 520 0, 1 etc. (increasing horizontally across each stripe). In the example, combined plane register C indicates that, for this particular LBA, plane 1, die 0, channel 0 is bad 530.

For each instruction sent to the flash device controllers to program a page the back-up engine also sets the cache bit 522 to "1b" (whose value is indicated in the bottom right of each box 510) to indicate that the following page in the same plane will be programmed.

Once commands have been sent to cover stripes 0, 1 and 2 500, 501, 502 the back-up engine waits for status on the commands for stripe 0 500. The nature of flash cache commands is such that the success or fail status of the previous command is only available after the current command has been sent. So in this example, the statuses of the page program commands for stripe 0 500 may only be available after the page program commands for stripe 1 501 have been sent. Since, each flash plane can handle up to two commands at a time, the back-up engine sends the stripe 2 502 program commands to the flash device controllers so that they can in turn be issued to the flash memory immediately after the stripe 1 501 commands have been sent and whilst the stripe 0 500 statuses are being returned. This is why the back-up engine may have up to three program commands outstanding for each plane. In this way, the flash memory is being kept as busy as possible servicing page program commands thus improving performance.

Once all the statuses for stripe 0 500 have been received the back-up engine determines whether any stripe 0 500 pages failed to program.

If no pages failed to program, then no update to map C is required and program commands for stripe 3 503 are sent to the same planes as for stripes 0, 1 and 2 with cache bit set as shown in FIG. 5B. The back-up engine then waits for all statuses for stripe 1 501 to be returned before deciding whether or not to write stripe 4. If no pages failed to program for stripe 1 501 then it may proceed to write stripe 5 and so on.

If one or more pages failed to program for stripe 0 500, then the back-up engine may update the grown bad plane register and also map C accordingly with the positions of the new bad planes.

In the example of FIG. 5C, plane 0, die 0, channel 0 540 returned bad status for that particular page program. The back-up engine then issues page program commands to the planes for stripe 3 503 but with the cache bit 523 reset to "0b". This may indicate to the flash device controllers that the pages of stripe 3 503 should be programmed with an "end cache" program command to end the sequence of cache commands. The back-up engine then waits for all statuses from stripes 1, 2 and 3 500, 501, 502 to return before issuing a re-write of stripes 0, 1 and 2 510, 511, 512 but avoiding the newly detected grown bad block 540 at plane 0, die 0, channel 0. The cache bit is set for the program commands of the re-written stripes.

Figure 6A:
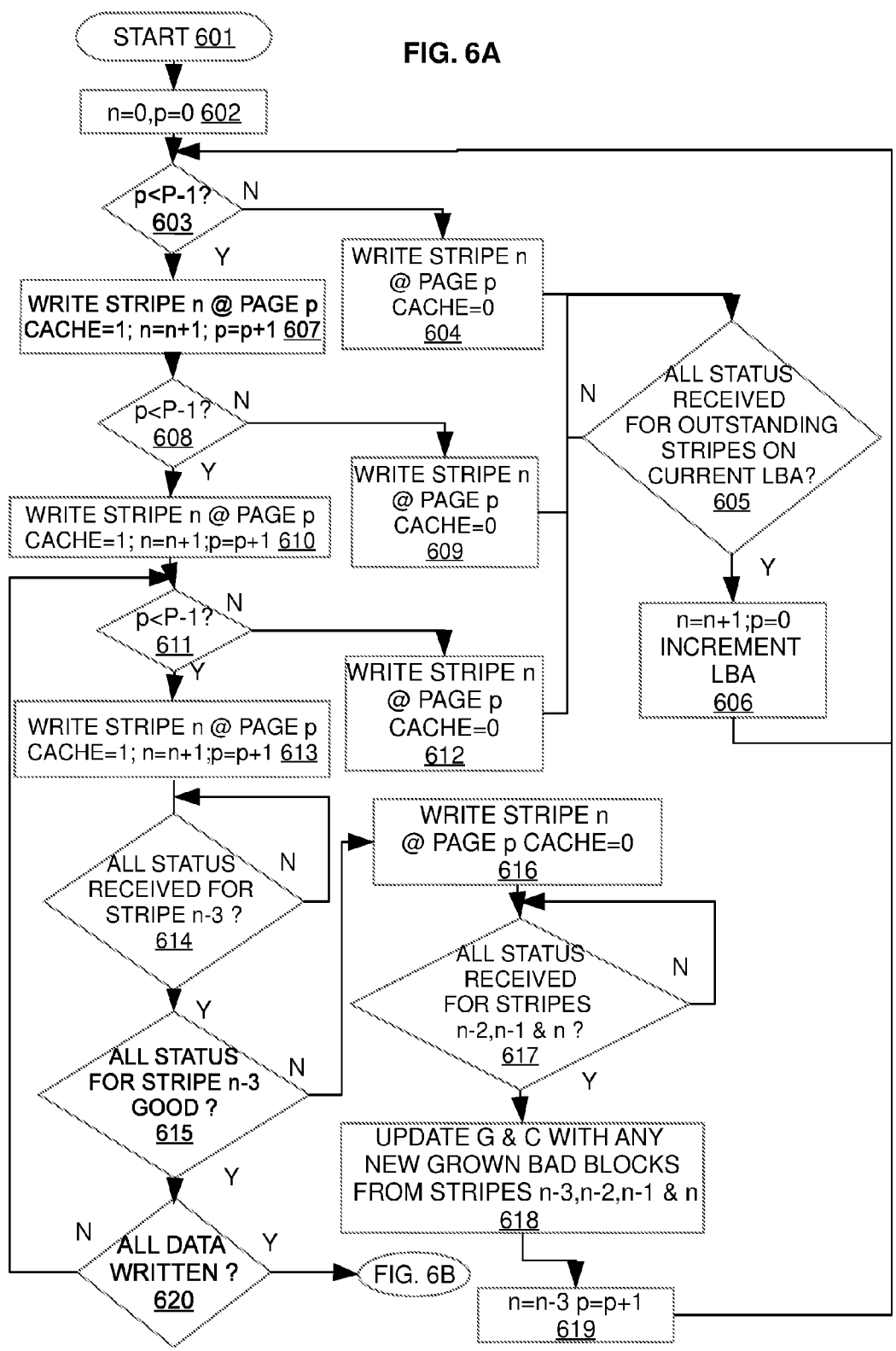
FIG. 6A is a flow diagram of a specific example of the method of FIG. 1A.

Referring to FIG. 6A, a flow diagram summarizes a specific example for carrying out the described back-up method as described in FIG. 1A. Note P represents the number of pages per block.

The method starts 601 with n=0, p=0 602, where n is a stripe and p is a page.

It is determined 603, if the current page is less than the page before the end of the block. If it is not, then the stripe is written 605 at the current page and the cache bit is set to "0" to indicate that the end of the block has been reached. It is then determined if all statuses have been received 605 for outstanding stripes on the current LBA. If so, the stripe is incremented, the page set to "0", and the LBA incremented 606. The method then loops to operation 603.

If at operation 603, it is determined that the current page is less than the page before the end of the block, then current stripe n is written 607 at the current page p, the cache bit is set to "1", and n and p are both incremented.

The method then repeats for this second stripe, and it is determined 608 if the current page is less than the page before the end of the block. If it is not, then the stripe is written 609 at the current page and the cache bit is set to "0" to indicate that the end of the block has been reached. It is then determined if all statuses have been received 605 for outstanding stripes on the current LBA. If so, the stripe is incremented, the page set to "0", and the LBA incremented 606. The method then loops to operation 603.

If at operation 608, it is determined that the current page is less than the page before the end of the block, then current stripe n is written 610 at the current page p, the cache bit is set to "1", and n and p are both incremented.

The method then repeats for this third stripe, and it is determined 611 if the current page is less than the page before the end of the block. If it is not, then the stripe is written 612 at the current page and the cache bit is set to "0" to indicate that the end of the block has been reached. It is then determined if all statuses have been received 605 for outstanding stripes on the current LBA. If so, the stripe is incremented, the page set to "0", and the LBA incremented 606. The method then loops to operation 603.

If at operation 611, it is determined that the current page is less than the page before the end of the block, then current stripe n is written 613 at the current page p, the cache bit is set to "1", and n and p are both incremented.

In this way, three stripes are written concurrently.

It is then determined 614, if all status have been received for the first stripe (n−3). If they have, it is determined 615 if all the status for this stripe are good.

If they are not good, a next stripe n is written 616 at page p, with the cache bit set to "0". It is determined 617 if all status are received for the three outstanding stripes, n−2, n−3, n. If so, the grown bad plane register and map C are updated 618 with any new grown bad blocks from stripes n−3, n−2, n−1 and n. n is set to n−3, and p to p+1 and the method loops to operation 603 to rewrite the stripes at a next page.

Figure 6B:
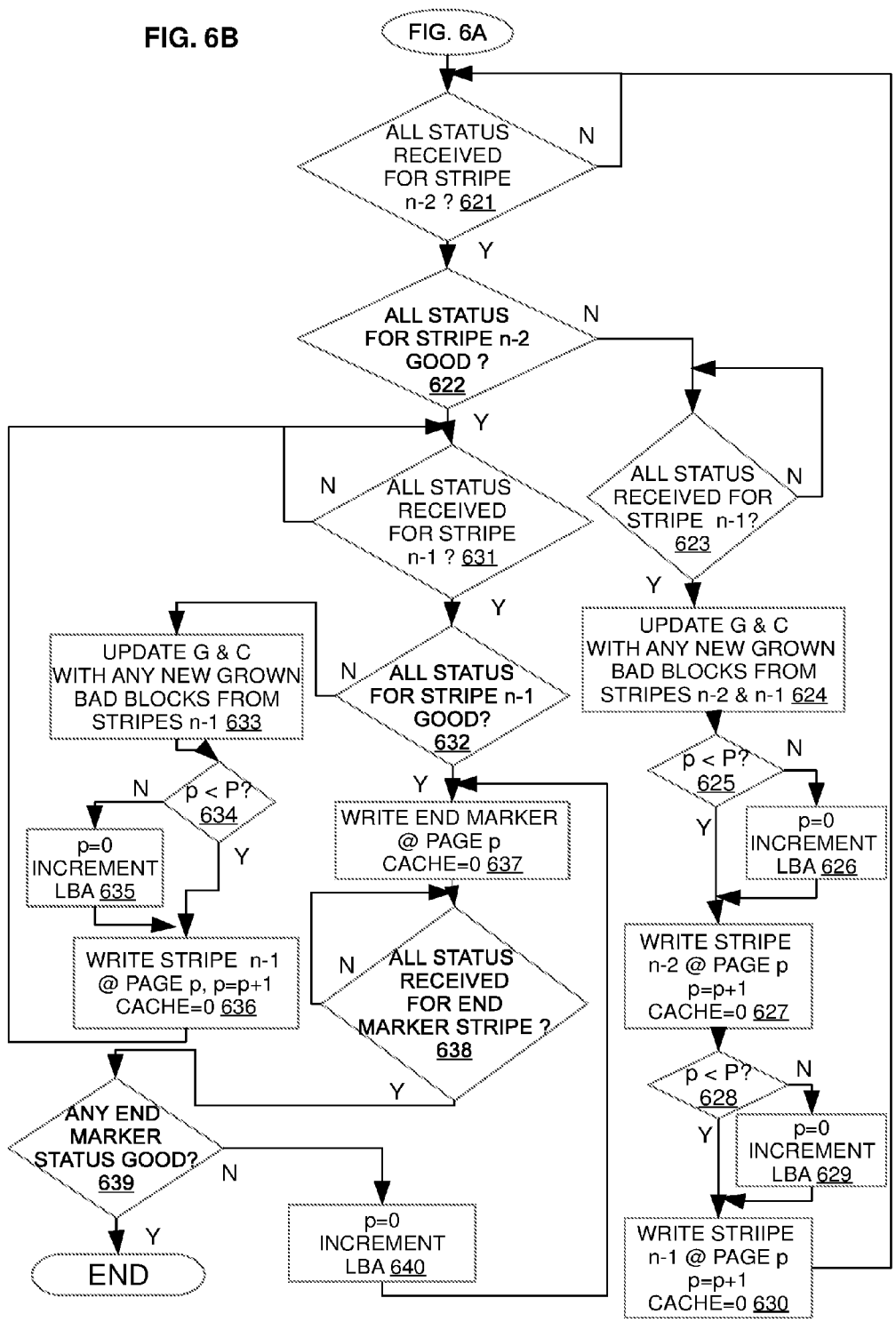
FIG. 6B is a flow diagram of a specific example of the method of FIG. 1B.

If it is determined at operation 615 that the status are all good for stripe n−3, it is determined 620 if all the data is saved, the method may proceed to the method shown in FIG. 6B.

Referring to FIG. 6B, a flow diagram summarizes a specific example for carrying out the described back-up method as described in FIG. 1B. This method continues from the step "A" in FIG. 6A.

It may be determined 621 if the all the statuses have been received for stripe n−2. If not, the method loops to wait for the statuses. Once all the statuses have been received, it may be determined 622 if all the statuses for stripe n−2 are good.

If the statuses are not all good, it is determined 623 if all the statuses have been received for stripe n−1. If not, the method loops to wait for the statuses. Once all the statuses have been received for stripe n−1, the grown bad plane register (G) and the combined map (C) are updated 624 with any new grown bad blocks from stripes n−2 and n−1.

It may be determined 625 if the page address about to be written is within the range of the block. If it is not, p is set to "0" and the LBA is incremented 626. In both cases, stripe n−2 is written 627 at page p and p is then incremented to p=p+1, and the cache bit is set to "0".

It may again be determined 628 if the page address about to be written is within the range of the block. If it is not, p is set to "0" and the LBA is incremented 629. In both cases, stripe n−1 is written 630 at page p and p is then incremented to p=p+1, and the cache bit is set to "0".

The method may then loop to operation 621 to wait for all statuses to be received for stripe n−2.

Continuing from operation 622, if it is determined that all the statuses for stripe n−2 are good, then it may be determined 631 if all the statuses for stripe n−1 have been received. If they have not yet all been received, the method loops to wait for them. Once they have all been received, it may be determined 632 if all the statuses for stripe n−1 are good.

If they are not all good, the grown bad plane register (G) and the combined map (C) are updated 633 with any new grown bad blocks from stripe n−1.

It may be determined 634 if the page address about to be written is within the range of the block. If it is not, p is set to "0" and the LBA is incremented 635. In both cases, stripe n−1 is written 636 at page p and p is then incremented to p=p+1, and the cache bit is set to "0". The method may then loop to operation 631 to await the statuses for stripe n−1.

If at operation 632 all the statuses for strip n−1 are good, an end marker stripe is written 637 at page p and a cache bit set to "0". It may be determined 638 if all statuses are received for the end marker stripe. If not, the method waits for the statuses to be received. Once all received, it is determined 639 if any of the statuses are good. If they are all bad, p may be set to "0" and the LBA incremented 640 and the method may loop to re-write 637 the end market stripe. If at operation 639 it is determined that any end marker status is good, the method may end.

When writing a stripe on the final page address of the LBA, the back-up engine must set the cache bit to 0 to ensure that the flash device controllers end the sequence of cache commands. This is because cache commands may only be done within an LBA.

Since the grown and known bad plane registers are embedded in the metadata of the dump image, the above algorithm can be applied when restoring data from flash memory. In this case, cache read commands are issued to those planes which the grown and known bad plane registers indicate to be good. The back-up engine would set the cache bit (based on these bitmaps) to indicate to the flash device controllers when to issue cache read commands and to which planes.

This described method has the advantage over known solutions to flash back up in that it can adapt to blocks that were discovered to be bad during the actual back up process. In addition, if an entire channel (i.e. flash device) were to fail the back up process could still continue. A complete channel failure would simply mean that all the pages belonging to that channel would be marked as bad in the grown bad pages map metadata fields of good pages in the back-up image. The described method would use the grown bad page maps to avoid reading from that channel in the same way that it avoided reading from a page in block n of a particular plane on a particular die on a particular channel After the restore is complete, the last page of each block in the back-up image could be read manually to determine where the grown bad planes in those blocks were. System firmware could then update its own bad block list so that these blocks can be avoided on future back-ups.

Figure 7:
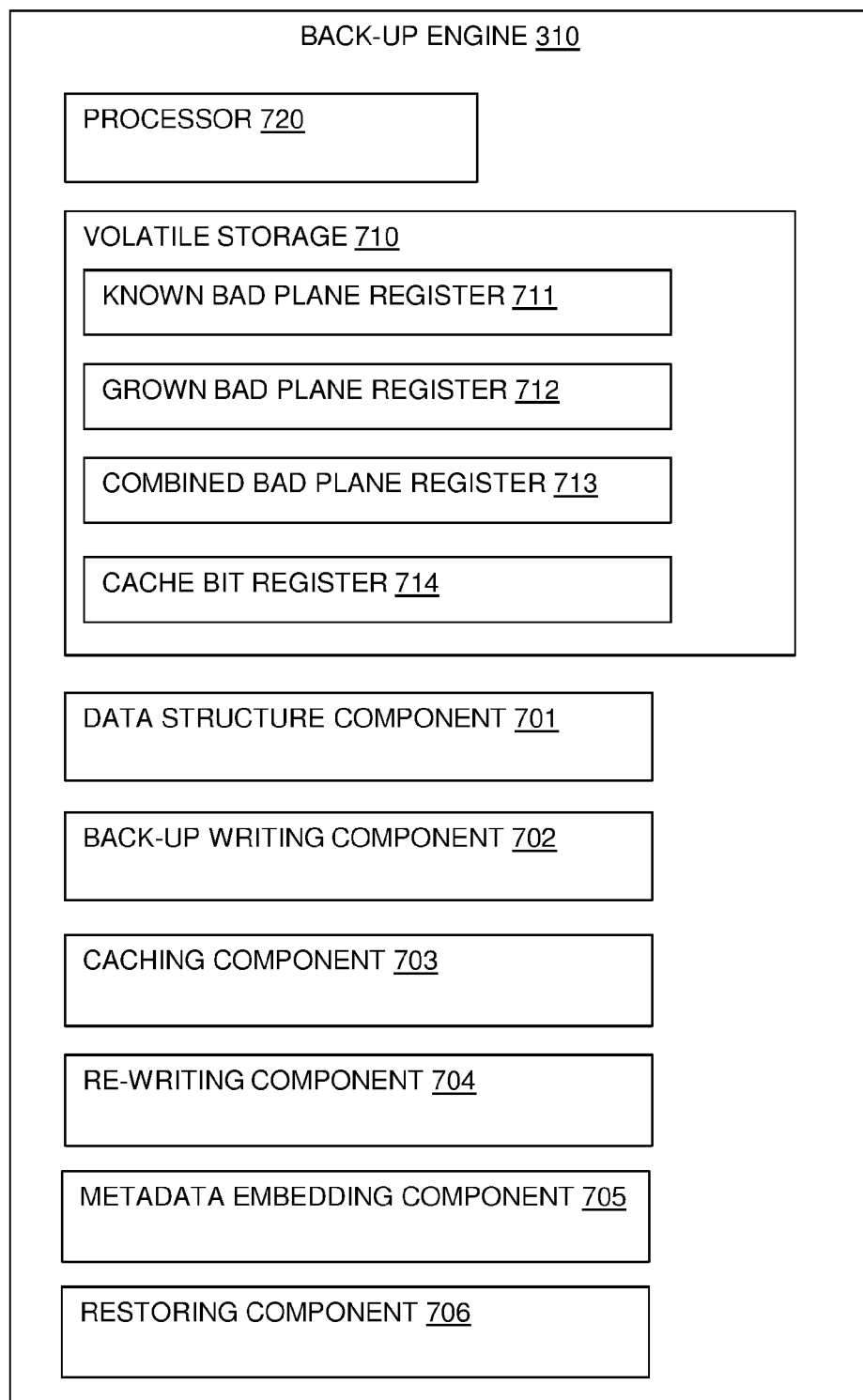
FIG. 7 is a block diagram of an example embodiment of a system in accordance with the present invention.

Referring to FIG. 7 a block diagram shows an example embodiment of a back-up engine 700 for a flash memory system.

The back-up engine 700 may have a processor 720 for backing-up data to flash memory formed of multiple flash devices. The back-up engine 700 may provide commands to multiple flash device controllers having dedicated flash interfaces to the multiple flash devices. The back-up engine 700 may be provided for backing-up data during a temporary period of power provided by a temporary power source such as a charged capacitor.

The back-up engine 700 may include software units providing functionality when executed by the processor of the back-up engine 700.

The back-up engine 700 may include data structure component 701 for organizing back-up data into stripes, wherein a stripe is a set of pages across all available flash memory devices, dies and planes which have the same block and page address.

A volatile storage 710 may be provided for storing metadata regarding the back-up process including a known bad plane register 711, a grown bad plane register 712, and a combined register 713 of all bad planes. A cache bit register 714 may also be provided. The volatile storage 710 may have a temporary power supply for use during the back-up process.

A back-up writing component 702 may be provided for using the metadata when writing back-up data to determine which planes to send cache program commands to.

A caching component 703 is provided for sending cache program commands to three or more stripes of data simultaneously including providing an indication in the stripe that the stripe is handling a cache program command.

A re-writing component 704 is provided for use if one or more grown bad blocks are encountered whilst saving a stripe of data, the re-writing component 704 re-writing the stripe of data to the next available page address avoiding the grown bad block.

The back-up engine 700 may include a metadata embedding component 705 for embedding bad block metadata in the backed-up data for use during restoration.

A restoring component 706 may be provided for restoring backed-up data from flash memory including reading metadata from a stripe of backed-up data and issuing cache read commands for planes for which the metadata is good. The restoring component 706 may include updating the volatile storage to store the metadata read from the backed-up data including locations of known bad planes and grown bad planes.

Figure 8:
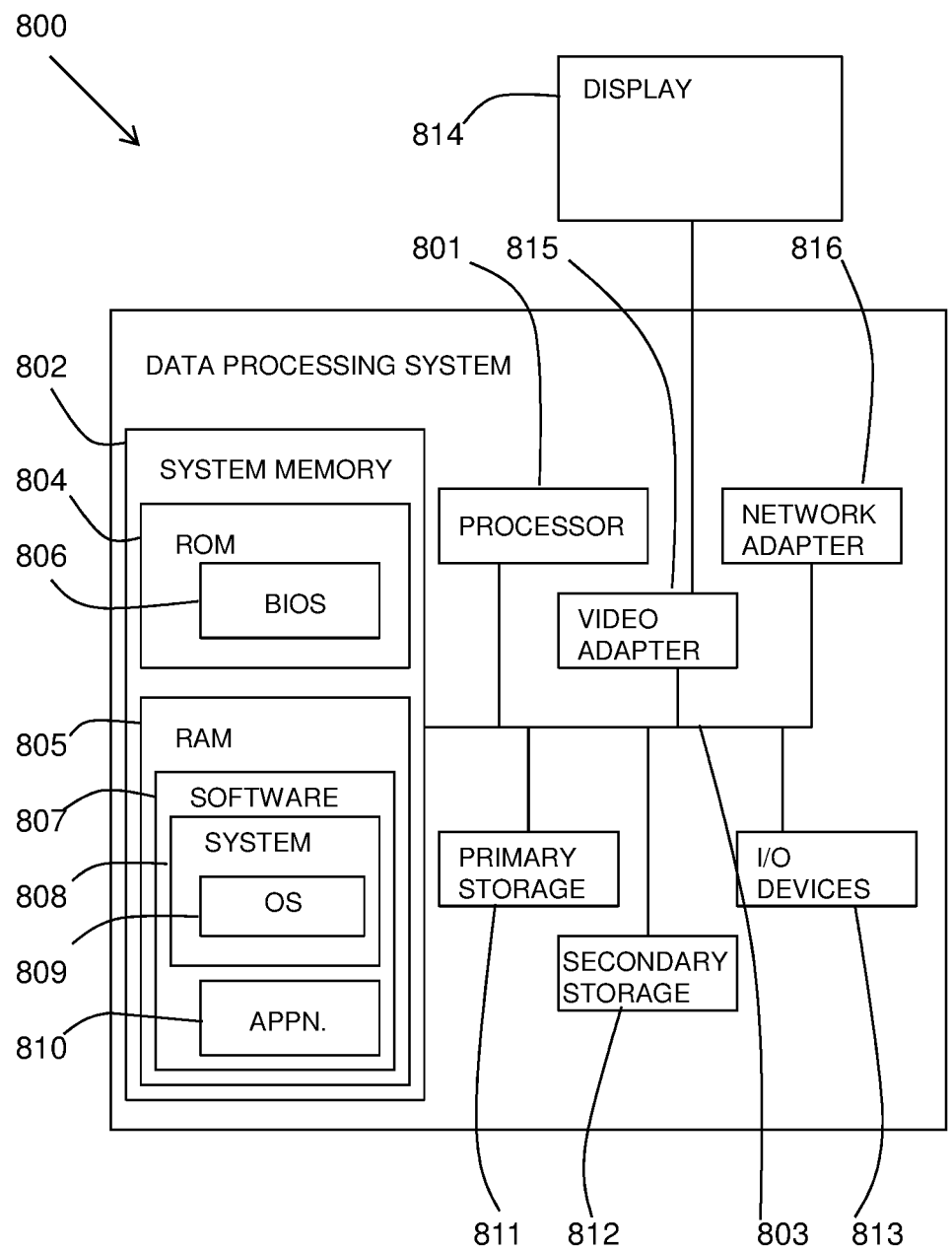
FIG. 8 is a block diagram of an embodiment of a computer system in which the present invention may be implemented.

Referring to FIG. 8, an exemplary system for implementing aspects of the invention includes a data processing system 800 suitable for storing and/or executing program code including at least one processor 801 coupled directly or indirectly to memory elements through a bus system 803. The memory elements may include local memory employed during actual execution of the program code, bulk storage, and cache memories which provide temporary storage of at least some program code in order to reduce the number of times code must be retrieved from bulk storage during execution.

The memory elements may include system memory 802 in the form of read only memory (ROM) 804 and random access memory (RAM) 805. A basic input/output system (BIOS) 806 may be stored in ROM 804. Software 807 may be stored in RAM 805 including system software 808 such as operating system software 809. Software applications 810 may also be stored in RAM 805.

The system 800 may also include a primary storage means 811 such as a magnetic hard disk drive and secondary storage means 812 such as a magnetic disc drive and an optical disc drive. The drives and their associated computer-readable media provide non-volatile storage of computer-executable instructions, data structures, program modules and other data for the system 800. Software applications may be stored on the primary and secondary storage means 811, 812 as well as the system memory 802.

The computing system 800 may operate in a networked environment using logical connections to one or more remote computers via a network adapter 816.

Input/output devices 813 may be coupled to the system either directly or through intervening I/O controllers. A user may enter commands and information into the system 800 through input devices such as a keyboard, pointing device, or other input devices (for example, microphone, joy stick, game pad, satellite dish, scanner, or the like). Output devices may include speakers, printers, etc. A display device 814 is also connected to system bus 803 via an interface, such as video adapter 815.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Improvements and modifications can be made to the foregoing without departing from the scope of the present invention.

What is claimed:

1. A method for controlling back-up of data to flash memory, comprising:
    organizing back-up data into stripes, wherein a stripe is a set of pages across all available flash memory devices, dies and planes which have the same block and page address;
    maintaining metadata indicating locations of known bad planes and grown bad planes;
    using the metadata when writing back-up data to determine which planes to send cache program commands to; and
    sending cache program commands to three or more stripes of data simultaneously including providing an indication in a stripe that the stripe is handling a cache program command;
    wherein if a grown bad block is encountered whilst saving a stripe of data, the stripe of data is re-written to the next available page address avoiding the grown bad block.

2. The method as claimed in claim 1, wherein providing an indication in a stripe being written that the stripe is handling a cache program command includes setting a bit in metadata indicating that the following page in the plane will also be programmed.

3. The method as claimed in claim 1, wherein maintaining metadata includes maintaining a combined bad plane register of known bad planes and grown bad planes, wherein the combined bad plane register carries out an OR operation of the known bad planes and the grown bad planes.

4. The method as claimed in claim 1, including for each plane a cache register allowing a host to move data in or out of flash memory whilst the flash memory is busy carrying out an array operation.

5. The method as claimed in claim 4, wherein sending cache program commands to three or more stripes of data simultaneously includes allowing a host to transfer data for a second page program whilst a plane is busy completing the previous page program.

6. The method as claimed in claim 1, including for each stripe determining if any pages have failed;
    if no pages have failed in a stripe, continue writing next stripe;
    if one or more pages have failed in a stripe, update the grown bad plane metadata for the three or more stripes, end a cache program in next stripe, and re-write the previous three or more stripes.

7. The method as claimed in claim 1, wherein maintaining metadata indicating locations of known bad planes and grown bad planes includes a known bad plane register, a grown bad plane register, and a combined register of all bad planes.

8. The method as claimed in claim 1, including embedding bad block metadata in the backed-up data for use during restoration.

9. The method as claimed in claim 1, further comprising restoring backed-up data from flash memory including reading metadata from a stripe of backed-up data, and issuing cache read commands for planes for which the metadata is good.

10. The method as claimed in claim 9, wherein restoring backed-up data from flash memory includes updating the metadata in the form known bad planes and grown bad planes from metadata embedded in the backed-up data in the flash memory.

11. A system for controlling back-up of data to flash memory, wherein the system includes a back-up engine having a processor for backing-up data to flash memory formed of multiple flash devices, wherein the back-up engine provides commands to multiple flash device controllers having dedicated flash interfaces to the multiple flash devices, the back-up engine comprising:
    a data structure component for organizing back-up data into stripes, wherein a stripe is a set of pages across all available flash memory devices, dies and planes which have the same block and page address;
    a volatile storage for storing metadata regarding the back-up process including maintaining metadata indicating locations of known bad planes and grown bad planes, wherein the volatile storage has a temporary power supply;
    a back-up writing component using the metadata when writing back-up data to determine which planes to send cache program commands to;
    a caching component for sending cache program commands to three or more stripes of data simultaneously including providing an indication in a stripe that the stripe is handling a cache program command; and a re-writing component, wherein if a grown bad block is encountered whilst saving a stripe of data, the stripe of data is re-written to the next available page address avoiding the grown bad block.

12. The system as claimed in claim 11, wherein the caching component includes providing an indication in a stripe being written that the stripe is handling a cache program command and setting a bit in metadata indicating that the following page in the plane will also be programmed.

13. The system as claimed in claim 11, wherein the volatile storage for storing metadata includes a combined bad plane register of known bad planes and grown bad planes, wherein the combined bad plane register carries out an OR operation of the known bad planes and the grown bad planes.

14. The system as claimed in claim 11, wherein the caching component includes, for each plane, a cache register allowing a host to move data in or out of flash memory whilst the flash memory is busy carrying out an array operation.

15. The system as claimed in claim 14, wherein the caching component configured to send cache program commands to three or more stripes of data simultaneously includes allowing a host to transfer data for a second page program whilst a plane is busy completing the previous page program.

16. The system as claimed in claim 11, the re-write component for each stripe determines if any pages have failed;

if no pages have failed in a stripe, the re-write component continues writing next stripe;

if one or more pages have failed in a stripe, the re-write component updates the grown bad plane metadata for three or more stripes, ends a cache program in next stripe, and re-writes the previous three or more stripes.

17. The system as claimed in claim 11, wherein the volatile storage for storing metadata indicating locations of known bad planes and grown bad planes includes a known bad plane register, a grown bad plane register, and a combined register of all bad planes.

18. The system as claimed in claim 11, including a metadata embedding component for embedding bad block metadata in the backed-up data for use during restoration.

19. The system as claimed in claim 11, further comprising a restoring component for restoring backed-up data from flash memory including reading metadata from a stripe of backed-up data, issuing cache read commands for planes for which the metadata is good.

20. The system as claimed in claim 19, wherein the restoring component includes updating the volatile storage to store the metadata read from the backed-up data including locations of known bad planes and grown bad planes.

\* \* \* \* \*